US008067663B2

(12) United States Patent
Bechert et al.

(10) Patent No.: US 8,067,663 B2
(45) Date of Patent: Nov. 29, 2011

(54) ABSORBENT SANITARY ARTICLE FOR ABSORBING BODY FLUID

(75) Inventors: Thorsten Bechert, Forchheim (DE); Peter Steinrucke, Erlangen (DE)

(73) Assignee: Bio-Gate AG, Nuremburg (DE)

( * ) Notice: Subject to any disclaimer, the term of this patent is extended or adjusted under 35 U.S.C. 154(b) by 182 days.

(21) Appl. No.: 12/488,012

(22) Filed: Jun. 19, 2009

(65) Prior Publication Data

US 2009/0275907 A1  Nov. 5, 2009

Related U.S. Application Data

(63) Continuation of application No. 11/716,984, filed on Mar. 12, 2007, now Pat. No. 7,910,796, which is a continuation of application No. 10/766,272, filed on Jan. 28, 2004, now abandoned.

(51) Int. Cl.
 *A61F 13/15* (2006.01)
(52) U.S. Cl. ......... 604/367; 604/359; 604/360; 604/365
(58) Field of Classification Search .................. 604/367, 604/359, 360, 365; 424/76.1–76.4, 618
See application file for complete search history.

(56) References Cited

U.S. PATENT DOCUMENTS

| 4,911,898 | A | * | 3/1990 | Hagiwara et al. ............ 423/700 |
| H1732 | H |  | 6/1998 | Johnson |
| 2005/0080157 | A1 |  | 4/2005 | Wagener et al. |
| 2005/0165372 | A1 |  | 7/2005 | Bechert et al. |
| 2006/0018943 | A1 |  | 1/2006 | Bechert et al. |
| 2007/0077312 | A1 |  | 4/2007 | Bechert et al. |
| 2007/0081958 | A1 |  | 4/2007 | Bechert et al. |
| 2007/0203442 | A1 |  | 8/2007 | Bechert et al. |

FOREIGN PATENT DOCUMENTS

| DE | 199 558 697 A1 | 6/2001 |
| EP | 1066825 A1 | 1/2001 |
| JP | 2003-052746 | 2/2003 |
| WO | WO 01/41819 A1 | 6/2001 |

OTHER PUBLICATIONS

Bernd H. Gunther: "Metal Nanopowders for Electrically Conductive Polymers", The International Journal of Powder Metallurgy, vol. 35, No. 7, 1999, pp. 53-58.
Stefan Kotthaus et al.: Study of Isotropically Conductive Bondings Filled with Aggregates of Nano-Sized Ag-Particles IEEE Transactions on Components, Packaging, and Manufacturing Technology—Part A, vol. 20, No. 1, Mar. 1997, pp. 15-20.
B. Gunther, et al.: Metal Nanopowders for Polymer Matrix Composites, 1998 PM World Congress Nanocrystalline Materials, Fraunhofer Institut for Applied Materials Research (IFAM), D 28717 Bremen, Germany, pp. 567-572.

* cited by examiner

*Primary Examiner* — Jacqueline F. Stephens
(74) *Attorney, Agent, or Firm* — Pearne & Gordon LLP

(57) ABSTRACT

Disclosed is an absorbent sanitary article for absorbing body fluids which comprises a matrix containing metallic silver, wherein the silver is present bound to a fiber 24 exclusively on the surface thereof.

43 Claims, 6 Drawing Sheets

ABSORBENT SANITARY ARTICLE FOR ABSORBING BODY FLUID

Figure 1A:
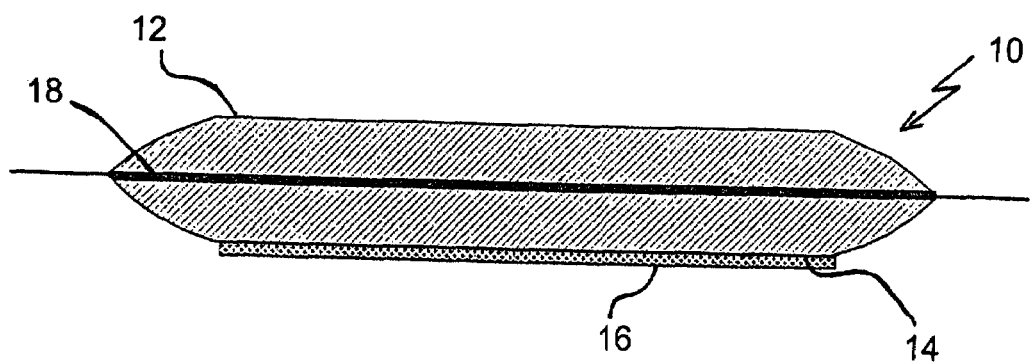

This invention relates to an absorbent sanitary article for absorbing body fluids which comprises a matrix containing metallic silver.

An absorbent sanitary article of the aforementioned kind is known from EP 1 066 825 A1. The sanitary article described therein typically comprises a solid matrix consisting of pulp in particular. Saturated with body fluid, the matrix constitutes a good substrate for a number of microorganisms. The growth of such microorganisms can give rise to sanitary and medical problems. It may lead to the development of unpleasant odors in particular.

The sanitary articles known from EP 1 066 825 A1 tackle this problem by including an organic matrix which contains homogeneously disbursed silver particles. The silver particles in question are from 1 to 50 nm in size. They are capable of releasing antimicrobially and fungicidally active silver ions. However, there is a problem in that at a high concentration silver ions also have a toxic effect on cells of human skin or mucosa. The silver particles in the sanitary article of EP 1 066 825 may be included in a solid or liquid organic matrix. The liquid organic matrix may be an oily liquid with which the sanitary product is treated. The disadvantage with this process is that the silver comes to be deposited in the sanitary article in a nondefined manner. The process may cause different amounts of silver particles to be utilized at a varying distance from the surface of the sanitary article. Consequently, the concentration of silver ions which is active at the surface of the sanitary article will also vary in use. Silver ion concentration at the surface may thus be high and hence cytotoxic effects may occur. It is further known that silver ions which have penetrated into a tissue or into a mucosal membrane may affect cell growth. This effect is undesirable for a sanitary article.

A further disadvantage of a liquid organic matrix is that silver particles may be flushed into deeper layers of the sanitary article in use of the sanitary article, so that it is no longer possible for the surface of the sanitary article to achieve an antimicrobially active silver ion concentration. This risk is particularly acute when large amounts of fluid have to be absorbed by the sanitary article, as in the case of diapers for example.

The solid organic matrix may be a polymer in which silver particles have been dispersed. Silver ion formation, however, is possible only from silver particles which are not fully encapsulated by the polymer and hence are accessible to the fluid. Consequently, more silver has to be incorporated into the polymer than is ultimately available for forming silver ions. The polymer has a further disadvantage in that those silver particles in the polymer which are inaccessible to the fluid may be haphazardly accessible to the fluid when the polymer becomes brittle or crumbly. Relatively large amounts of silver ions may then be unintentionally released, so that cytoxic effects may occur.

It is an object of the present intention to remedy prior art disadvantages. More particularly, a sanitary article containing metallic silver shall be provided that permits a more constant silver ion concentration at its body-facing surface in use for the duration of the typical use than sanitary articles known from EP 1066 825 A1. It is a further object of the present invention to provide a sanitary article where the concentration of silver ions at any one of its body-facing surfaces in use of the sanitary article end-product is kept so low that silver ions cannot pass into tissue or mucosa in an amount in which they would affect cell growth there.

According to the invention there is provided an absorbent sanitary article for absorbing body fluids which comprises a matrix containing metallic silver, wherein the silver is present bound to a fiber exclusively on the surface thereof. Bound is to be understood as meaning that the metallic silver is chemically or physically attached to the surface such that it cannot be flushed away from the fiber in use of the sanitary article end-product. Attachment may be via charges for example. A suitable silver-coated fiber is available for example from Statex Produktions-+Vertriebs GmbH, Querlandstr. 6b, 28357 Bremen, Germany. Surprisingly, the desirable antimicrobial and fungicidal effects are achievable with the inventive sanitary article at very low levels of silver. The immobilization of the metallic silver on the fiber makes it possible for the metallic silver to be disposed at a defined location within the sanitary article. This makes it possible to achieve a defined maximum silver ion concentration on the sanitary article surface which faces the body in use. Since the metallic silver is situated only at the surface of the fiber, the manufacturing process does not have to utilize an unnecessary amount of metallic silver which ultimately is completely surrounded by a polymer and thus is not accessible to body fluid.

Advantageously, the metallic silver is attached in depressions in the surface of the fiber, especially hind-grippedly. Such a fiber is available from Statex Produktions-+Vertriebs GmbH.

Preferably, the fiber is a synthetic fiber. The synthetic fiber may be a polyamide, such as nylon-6,6 or nylon-6, a polyester, such as Dacron, Diolen or Trevira, a polyacrylic, such as acrylic, Dralon, Dolan or Orlon, an elastane, such as Dorlastan or Lycra, or a polychloride, such as Movil or Rhovyl.

The fiber may be present in the form of a woven, in the form of a nonwoven or in the form of a thread. A thread may be a twisted fiber for example. An advantage here would be that the fiber is as a result easier to dispose at a defined location within the absorbent sanitary article. Suitable silver-containing wovens are likewise available from Statex Produktions-+Vertriebs GmbH. Such wovens are typically used for electrical screening and for producing conductive floors.

In a preferred embodiment, the fiber has a weight-based silver content of not more than 3%. This has the advantage that any cytotoxic effect and undesirable side-effects can be substantially ruled out. A further advantage is that the low silver content allows for a more skin-colored coloration of the fiber. The fiber surface would be metallically shiny at high silver contents. As a result, the sanitary article would be undesirably visible through light clothes.

Preferably, the silver content of the fiber is just high enough to ensure that an antimicrobial effect is detectable on a first body contact surface of the sanitary article for not more than 24 hours in particular. The requisite silver content is dependent inter alia upon the material of the fiber and upon the size of the metallic silver surface area accessible to body fluid. To detect the effect, the sanitary article is moistened with an amount of liquid which the sanitary article would typically absorb when put to its intended use. Preferably, the metallic silver is present in the form of bound particles from 1 to 30 nm, preferably from 1 to 10 nm and especially from 1 to 6 nm in diameter. The smaller the particles, the larger the surface area of the metallic silver. Any desired silver ion release is achievable with smaller particles at a lower amount of silver on account of the overall larger surface area.

In a preferred embodiment, the metallic silver fully surrounds the outer surface of the fiber. However, the outer surface is to be understood as not including the ends of the fiber which are bared by a cut through the fiber for example and which can each be free of silver. Such a fiber is available for example from Statex Produktions-+Vertriebs GmbH. Such a fiber has the advantage that the silver is particularly firmly adherent thereto.

In a preferred embodiment, the fiber, the woven, the nonwoven or the thread is present within the sanitary article in piecewise disbursement. The pieces in question have such a size that they are not flushed away by body fluid in the customary use of the sanitary article. Preferably, the fiber, the woven, the nonwoven or the thread is disposed within a layer of the sanitary article. In the case of a tampon, for example, this layer may be provided through a rolled woven within the tampon. As a result of the layer having a defined distance from the first surface, the position and the silver content of the layer can be used to determine the silver ion concentration which is possible at the first surface. Advantageously, the layer is disposed closer to the first surface of the sanitary article than to a second surface which is not intended for body contact, especially closer to the first surface than to the midpoint between the first surface and the second surface. The closer the layer is disposed to the first surface, the lower the silver contents which are sufficient for an antimicrobial and fungicidal effect on the first surface. On the other hand, disposition directly at the first surface will increase the risk that silver ions will enter a tissue or a mucosa and lead to undesirable side-effects there.

Preferably, the sanitary article contains a pulp and/or a superabsorbent. The sanitary article may be a disposable article. The disposable article may be a diaper, especially a pants-type diaper, a training pant, an incontinence pad or a feminine hygiene article, especially a sanitary napkin, a panty liner or a tampon. A training pant is an absorbent underpant worn by children undergoing toilet training.

The invention further provides a process for producing an absorbent sanitary article for absorbing body fluids which comprises a matrix containing metallic silver, which comprises the silver being bound to a fiber exclusively on the surface thereof. The silver may be applied to the fiber by electro, chemical or electrochemical deposition or by vapor deposition. Preferably, the silver is bound to the fiber by means of a chemical or physical bond. This may take the form of electrical charges for example. Similarly, lodging and attachment in fiber crypts is possible. Preferably, the metallic silver is attached in depressions in the surface, especially hind-grippedly. The surface of the fiber may be mordanted prior to the binding of the silver. Mordanting is where the surface is chemically modified, by means of a gas or liquid, in such a way that it is suitable for binding silver.

The fiber used is preferably a synthetic fiber. This synthetic fiber may contain in particular a polyamide, a polyester, a polyacrylic, an elastane or a polychloride. Preferably, the fiber is incorporated in the sanitary article in the form of a woven, in the form of a nonwoven or in the form of a thread.

In a preferred embodiment, the silver is applied up to a 3% silver content of the fiber. It is particularly advantageous to apply the silver only up to a silver content of the fiber just high enough to ensure that an antimicrobial effect is detectable on a first body contact surface of the sanitary article for not more than 24 hours in particular. The metallic silver may be bound in the form of particles from 1 to 30 nm, preferably from 1 to 10 nm and especially from 1 to 6 nm in diameter.

It is particularly advantageous for the metallic silver to be applied such that the outer surface of the fiber is fully surrounded by silver. But the ends of the fiber, for example, due to a cut through the fiber, may be free of silver. The ends are not outer surface for the purposes of the present invention.

The fiber, the woven, the nonwoven or the thread may be disbursed within the matrix of the sanitary article in piecewise form. Preferably, the woven, the nonwoven or the thread is disposed within a layer of the sanitary article. The layer is disposed closer to the first surface of the sanitary article than to a second surface which is not intended for body contact, especially closer to the first surface than to the midpoint between the first surface and the second surface. Preferably, a pulp and/or a superabsorbent is incorporated in the sanitary article.

Figure 2:
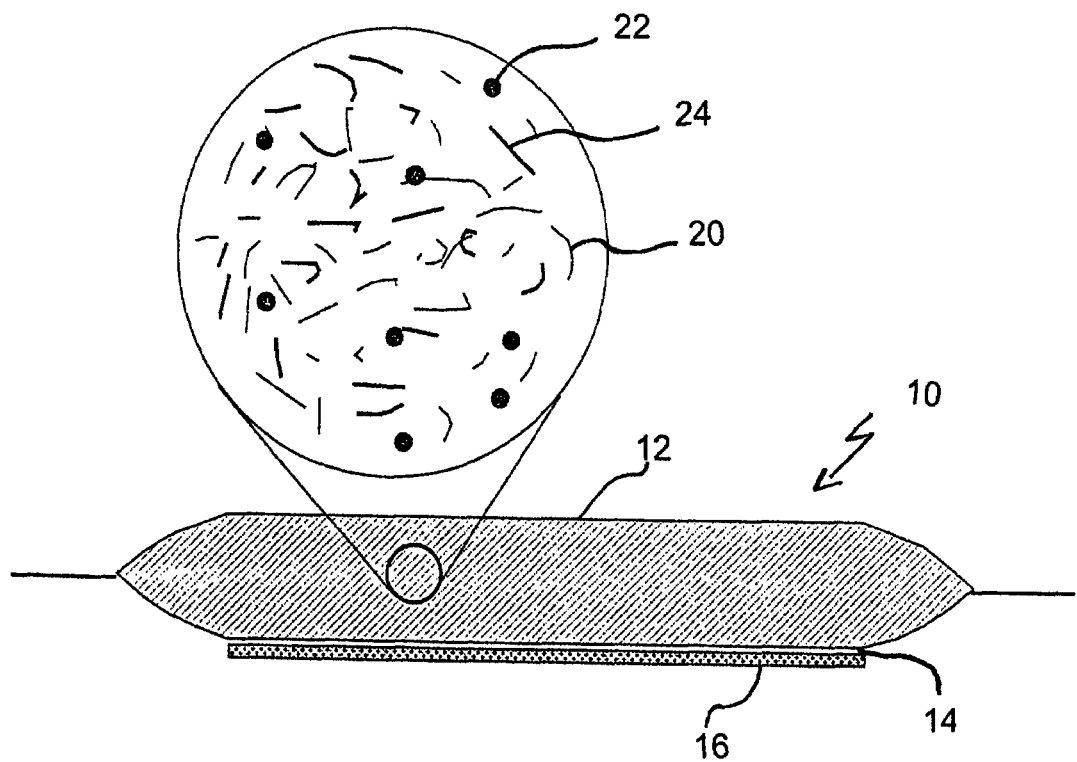
Figure 3:
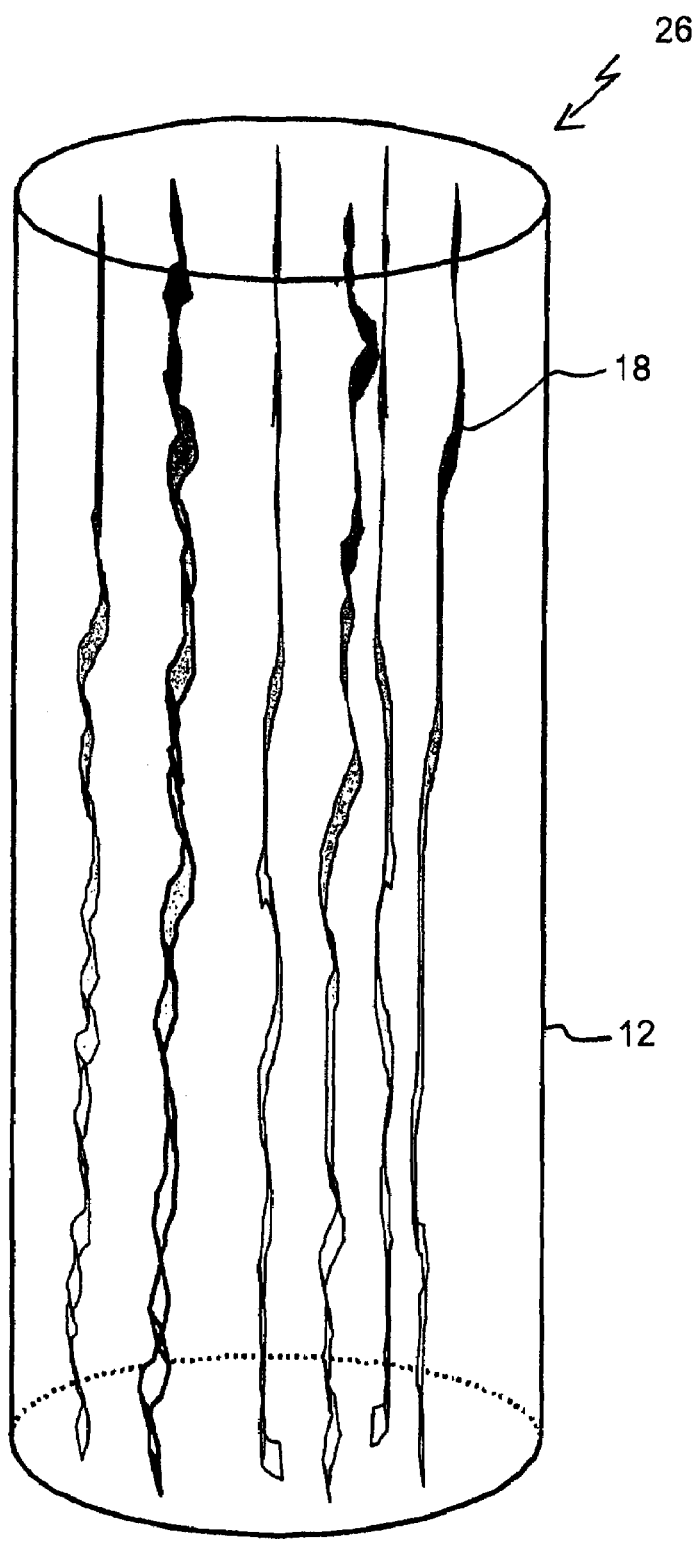
Figure 4:
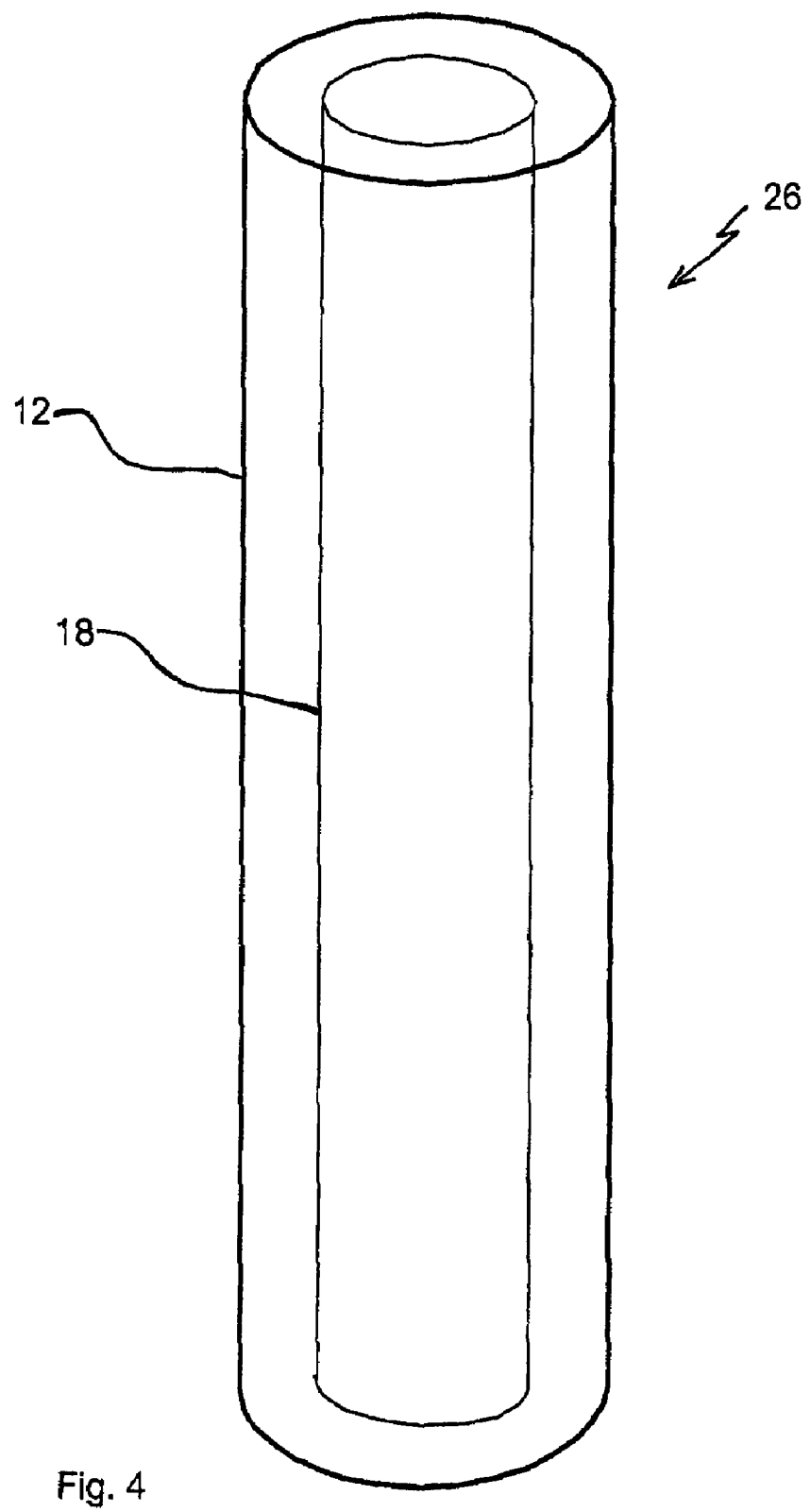
Figure 5:
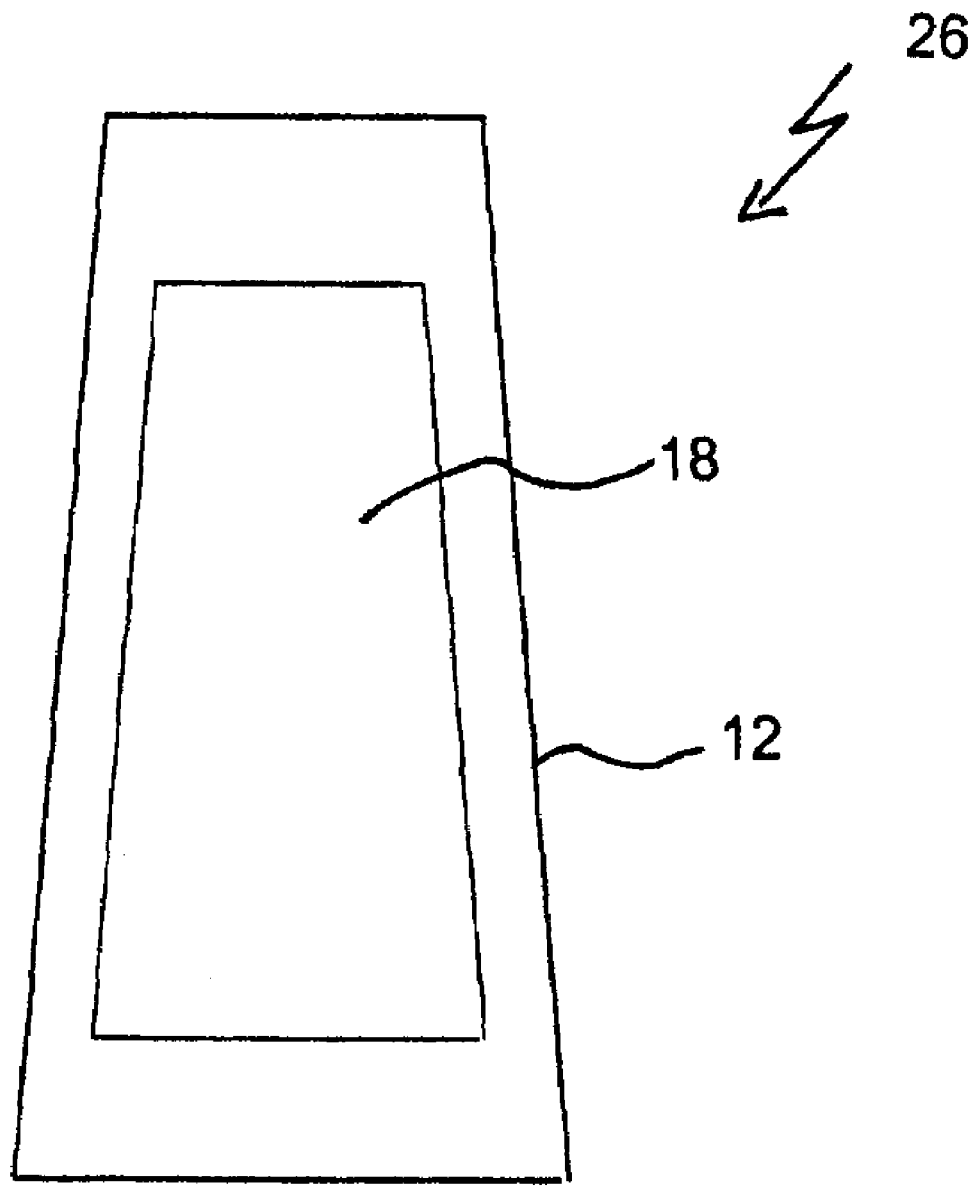
Figure 6:
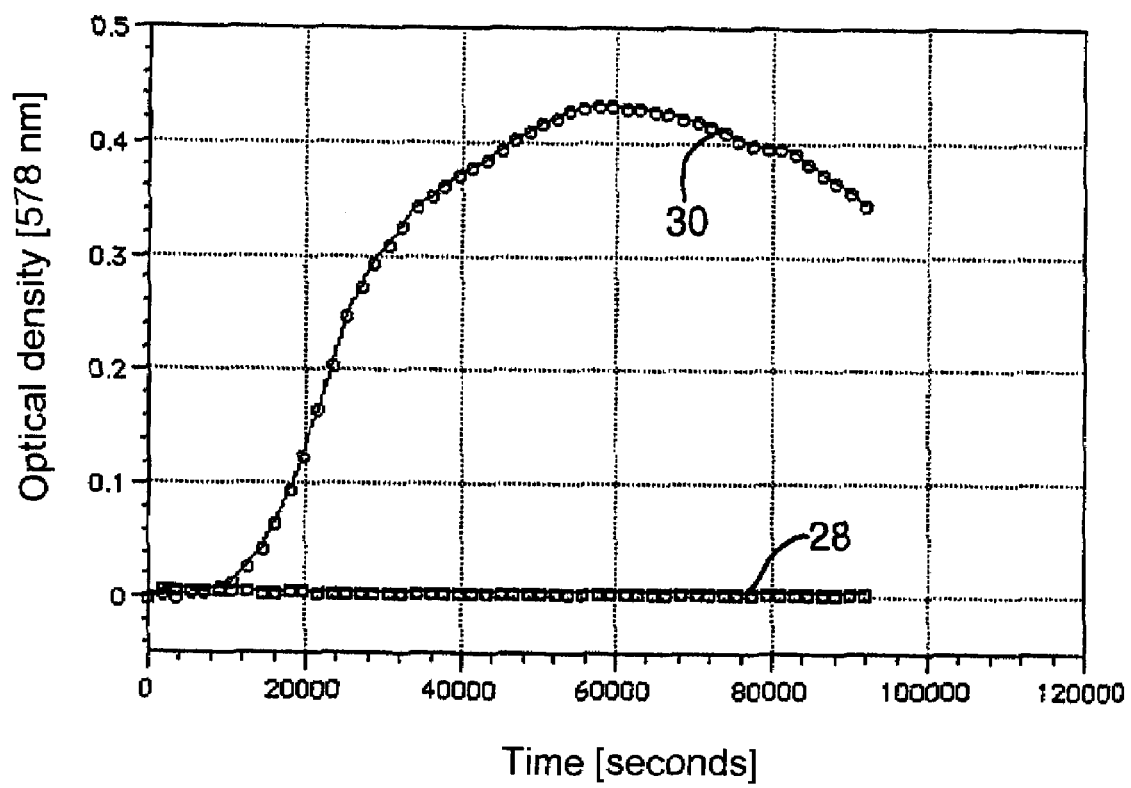

The invention will now be more particularly described with references to operative examples and the drawings, where FIGS. 1a and b show a schematic sectional depiction through a sanitary napkin having a layer of a silverized woven, FIG. 2 shows a schematic sectional depiction through a sanitary napkin having a silverized fiber present therein in piecewise disbursement, FIG. 3 shows a schematic perspective depiction of a tampon having silverized woven tapes passing therethrough, FIG. 4 shows a schematic perspective depiction of a tampon containing a silverized rolled woven ply, FIG. 5 shows a schematic sectional depiction of a cross section through a tampon having a silverized rolled woven ply, and FIG. 6 shows a graphic depiction of the growth of bacteria on a silverized woven and on a woven without silver.

FIG. 1a schematically depicts in cross section a sanitary napkin 10 which has a first body contact surface 12 and a second nonbody contact surface 14. The second surface 14 has been provided with an adhesive strip 16 which permits fastening, for example in a pair of panties. A layer of a silver-containing woven 18 is disposed in the center of the sanitary napkin. The woven 18 consists of nylon-6,6 fibers having silver bound to their surface.

Figure 1B:
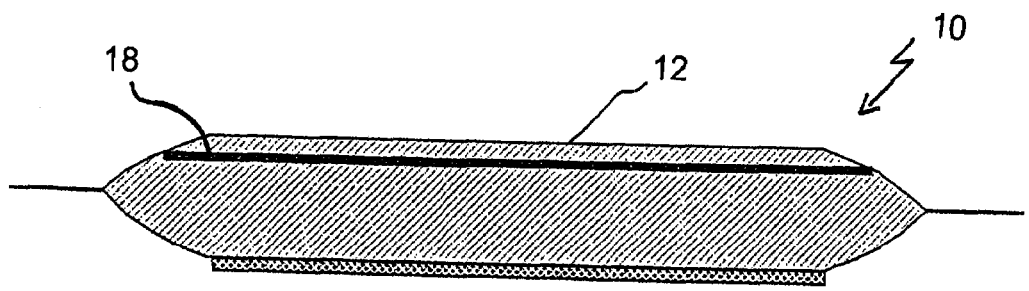

FIG. 1b shows a cross section through a similarly constructed sanitary napkin where the layer of the silverized woven 18 is disposed in the vicinity of the first surface 12. A silver ion concentration which is antimicrobially active at the first surface 12 can with this arrangement be achieved at a lower silver content than in the case of the sanitary napkin 10 as per FIG. 1a. This is because the silver ions released by the woven have to overcome a shorter diffusion path to get to the first surface 12. The advantage of the arrangement as per FIG. 1a, in contrast, is that a sufficiently high silver ion concentration to reliably prevent the growth of microorganisms is more likely to be achievable in the entire sanitary napkin even on absorption of a larger amount of fluid FIG. 2 shows a schematic depiction of a cross section through a sanitary napkin having a first surface 12, a second surface 14 and an adhesive strip 16. The portion which has been magnified is a schematic depiction of the composition of a matrix forming the filling of the sanitary napkin. The matrix contains pulp fibers 20, superabsorbents 22 and a silverized fiber 24 present therein in piecewise disbursement.

FIG. 3 shows a schematic perspective depiction of a tampon 26 having a first surface 12. This tampon 26 has narrow tapes of a silverized woven 18 passing through it.

FIG. 4 shows in schematic form a perspective depiction of a tampon 26 having a first surface 12, this tampon 26 containing a rolled silverized woven 18.

FIG. 5 shows in schematic form a cross section through a conically shaped tampon 26 having a first surface 12 and a rolled silverized woven 18 included therein.

The antimicrobial effect has been examined as per the method described in Bechert et al., NATURE MEDICINE Vol. 6 Issue 9, September 2000, pages 1053-1056, by means of bacteria of the type *Staphylococcus epidermidis* on a silverized woven and, for comparison therewith, on a woven without silver. The woven is a nylon-6,6 woven from Statex Produktions-+Vertriebs GmbH. In this woven, the silver is immobilized on the surface of the nylon-6,6 fiber.

FIG. 6 shows the line 28 of the time course of the bacterial growth on the silverized woven. The time course of bacterial growth on the woven without silver is depicted by line 30. The growth took place under almost physiological conditions in a phosphate-buffered salt solution. The line 28 shows complete inhibition of bacterial growth by the silverized woven.

What is claimed is:

1. An absorbent sanitary article for absorbing body fluids which comprises a fibrous matrix including at least one fiber having an outer surface and metallic silver attached to the outer surface, the silver having a metallic silver surface area, attachment of the silver to the outer surface consisting essentially of chemical and/or physical bonds other than bonds formed by liquid matrix or dispersing media for the silver, whereby the silver is immobilized relative to the fiber surface so that the metallic silver surface area is accessible to the body fluids and the silver cannot be flushed away from the fiber during use of the sanitary article.

2. An absorbent sanitary article according to claim 1, wherein said silver directly contacts said outer surface to form said chemical and/or physical bonds.

3. An absorbent sanitary article according to claim 2, wherein said silver is exclusively attached to said outer surface only and said sanitary article is substantially free of liquid matrix or dispersing media for the silver.

4. An absorbent sanitary article according to claim 2, wherein said silver is in the form of particles that directly contact the outer surface and are directly attached to the outer surface without intervening liquid matrix or dispersing media securing or attaching silver to the fiber surface during use of the sanitary article.

5. An absorbent sanitary article according to claim 1, wherein said sanitary article end-product during use is substantially free of liquid matrix or dispersing media for the silver.

6. An absorbent sanitary article according to claim 1, wherein said outer surface includes depressions and the outer surface extends into the depressions, and said silver is attached to the outer surface including the outer surface in the depressions.

7. An absorbent sanitary article according to claim 1, wherein said fiber is a synthetic fiber formed of a polymer selected from the group consisting of polyamides, polyesters, polyacrylics, elastanes and polychlorides.

8. An absorbent sanitary article according to claim 7, wherein said synthetic fiber is present in the form of a discrete fiber, a woven, a non-woven or a thread, said silver is present in the form of attached particles from 1 to 30 nm in diameter and in an amount equal to about 3% of the fiber weight, and said silver directly contacts said outer surface to form said chemical and/or physical bonds.

9. An absorbent sanitary article according to claim 1, wherein said silver is present in an amount equal to about 3% of the fiber weight.

10. An absorbent sanitary article according to claim 1, wherein said silver is present in the form of particles from 1 to 30 nm in diameter that are attached in direct contact with said outer surface.

11. An absorbent sanitary article according to claim 1, wherein said silver is present in the form of particles from 1 to 6 nm in diameter that are attached in direct contact with said outer surface.

12. An absorbent sanitary article according to claim 1, wherein said silver fully surrounds the outer surface of the fiber and said chemical and/or physical bonds result from electro, chemical or electrochemical deposition or vapor deposition.

13. An absorbent sanitary article according to claim 1, wherein the sanitary article is constructed as a disposable article, a diaper, a pants-type diaper, a training pant, an incontinence pad, a feminine hygiene article, a sanitary napkin, a panty liner or a tampon.

14. An absorbent sanitary article according to claim 1, wherein said fiber is in the form of discrete fibers, woven fibers, non-woven fibers or threads dispersed piecewise in the fibrous matrix of the sanitary article or disposed within a layer in the fibrous matrix of the sanitary article.

15. An absorbent sanitary article according to claim 14, wherein said fibers are disposed in said layer, said sanitary article fibrous matrix includes a first article surface intended for body contact and a second article surface not intended for body contact, and the layer is disposed closer to the first article surface.

16. An absorbent sanitary article according to claim 15, wherein the layer is closer to the first article surface than to the mid-point between the first article surface and the second article surface.

17. An absorbent sanitary article according to claim 1, wherein said sanitary article fibrous matrix includes pulp and/or superabsorbent.

18. An absorbent sanitary article for absorbing body fluids comprising a fibrous matrix including at least one fiber having an outer surface, metallic silver bonded to the outer surface by bonds that are free of liquid matrix or dispersing media for the silver, the silver having a metallic silver surface area, whereby the metallic silver surface area is accessible to the body fluids and the silver cannot be flushed away from the outer surface during use of the sanitary article.

19. An absorbent sanitary article according to claim 18, wherein said silver directly contacts said outer surface and said bonds are physical and/or chemical bonds.

20. An absorbent sanitary article according to claim 19, wherein said bonds result from electro, chemical or electrochemical deposition or vapor deposition.

21. An absorbent sanitary article according to claim 20, wherein said sanitary article is substantially free of liquid matrix or dispersing media for the silver.

22. An absorbent sanitary article according to claim 21, wherein said fiber is present in the form of a discrete fiber, a woven, a non-woven or a thread, and said silver is present in the form of bound particles from 1 to 30 nm in diameter and in an amount equal to about 3% of the fiber weight.

23. A process for producing an absorbent sanitary article for absorbing body fluids which comprises a fibrous matrix containing metallic silver having a metallic silver surface area, comprising the steps of disposing a fiber having an outer surface in said matrix, attaching the silver to the outer surface with bonds consisting essentially of chemical and/or physical bonds other than bonds formed by liquid matrix or dispersing media for the silver, and thereby immobilizing the silver relative to the outer surface of the fiber so that the metallic silver surface area is accessible to the body fluids and the metallic silver cannot be flushed away from the outer surface during use of the sanitary article.

24. A process according to claim 23, wherein the step of attaching the silver to the outer surface includes applying silver to the outer surface by electro, chemical or electrochemical deposition or by vapor deposition.

25. A process according to claim 23, wherein the sanitary article is substantially free of liquid matrix or dispersing media securing or attaching silver to the outer surface.

26. A process according to claim 23, wherein said outer surface includes depressions and outer surface extends into the depressions, and the silver is attached to the outer surface including the outer surface in the depressions.

27. A process according to claim 23, wherein the step of attaching the silver to the outer surface includes fully surrounding said fiber with silver attached to the outer surface.

28. A process according to claim 23, wherein the fiber is in the form of discrete fibers, woven fibers, non-woven fibers or threads disbursed within the sanitary article in piecewise form or disposed within a layer of the sanitary article.

29. A process for producing an absorbent sanitary article for absorbing body fluids which comprises a fibrous matrix containing metallic silver having a metallic silver surface area, comprising the steps of disposing a fiber having an outer surface in said matrix and binding said metallic silver exclusively to said fiber surface to immobilize the metallic silver relative to the surface of the fiber so that the metallic silver surface area is accessible to the body fluids and the metallic silver cannot be flushed away from the fiber surface during use of the sanitary article.

30. A process according to claim 29, wherein the binding step includes applying silver to the fiber surface by electro, chemical or electrochemical deposition or by vapor deposition.

31. A process according to claim 30, wherein the silver is bound to the fiber by means of a chemical or physical bond.

32. A process according to claim 29, wherein the fiber surface includes depressions and fiber surface extends into the depressions, and the metallic silver is attached to the fiber surface including the fiber surface in the depressions.

33. A process according to claim 29, further including binding said metallic silver only to said fiber outer surface and thereby providing the sanitary article end-product substantially free of liquid matrix or dispersing media.

34. A process according to claim 29, wherein the fiber is a synthetic fiber.

35. A process according to claim 29, wherein the silver is applied at a weight of up to a 3% based on the weight of the fiber.

36. A process according to claim 29, wherein the silver is only applied at a weight just high enough to ensure that an antimicrobial effect is detectable for not more than 24 hours on a first body contact surface of the sanitary article.

37. A process according to claim 29, wherein the metallic silver is bound in the form of particles from 1 to 30 nm in diameter.

38. A process according to claim 29, wherein the metallic silver is applied such that the outer surface of the fiber is fully surrounded by silver.

39. A process according to claim 29, wherein at least one of a pulp and a superabsorbent is incorporated in the sanitary article.

40. A process according to claim 29, characterized in that the fiber is in the form of discrete fibers, woven fibers, non-woven fibers or threads dispersed within the sanitary article in piecewise form.

41. A process according to claim 29, characterized in that the fiber is in the form of discrete fibers, woven fibers, non-woven fibers or threads is disposed within a layer of the sanitary article.

42. A process according to claim 41, characterized in that said sanitary article includes a first article surface intended for body contact, and a second article surface not intended for body contact, and the layer is disposed closer to the first surface.

43. A process according to claim 42, characterized in that the layer is closer to the first article surface than to the midpoint between the first article surface and the second article surface.

* * * * *

UNITED STATES PATENT AND TRADEMARK OFFICE
CERTIFICATE OF CORRECTION

PATENT NO.         : 8,067,663 B2                    Page 1 of 1
APPLICATION NO.    : 12/488012
DATED              : November 29, 2011
INVENTOR(S)        : Thorsten Bechert et al.

It is certified that error appears in the above-identified patent and that said Letters Patent is hereby corrected as shown below:

On the Title page of the patent, insert:

-- Foreign Application Priority Data

Feb. 11, 2002   (DE)   10205600.5 --

Signed and Sealed this
Fourteenth Day of February, 2012

David J. Kappos
*Director of the United States Patent and Trademark Office*